United States Patent [19]

Hoey

[11] 4,146,027

[45] Mar. 27, 1979

[54] METHOD FOR DRESSING A WOUND

[75] Inventor: Charles E. Hoey, Marlton, N.J.

[73] Assignee: Rohm and Haas Company, Philadelphia, Pa.

[21] Appl. No.: 794,770

[22] Filed: May 9, 1977

Related U.S. Application Data

[60] Continuation-in-part of Ser. No. 726,716, Sep. 24, 1976, Pat. No. 4,069,366, which is a division of Ser. No. 394,601, Sep. 5, 1973, Pat. No. 3,901,240, which is a continuation-in-part of Ser. No. 354,062, Apr. 24, 1973, Pat. No. 3,887,408.

[51] Int. Cl.² .............................................. A61L 15/00
[52] U.S. Cl. ..................................... 128/156; 428/311
[58] Field of Search ........................ 428/311, 310, 315; 128/155, 156

[56] References Cited

U.S. PATENT DOCUMENTS

| | | | |
|---|---|---|---|
| 3,648,692 | 3/1972 | Wheeler | 428/311 |
| 3,849,238 | 11/1974 | Gould et al. | 428/315 |

*Primary Examiner*—William J. Van Balen
*Attorney, Agent, or Firm*—Terence P. Strobaugh; Robert A. Doherty; George W. F. Simmons

[57] ABSTRACT

A procedure is provided for producing a wound dressing having a crushed or uncrushed foam bonded to a woven, knit or nonwoven absorbent layer, particularly woven cotton gauze. The foam is self-bonded to the absorbent layer, i.e., no adhesive is needed to bond the foam. The foam may be applied by one of several methods. One procedure comprises applying a thin layer of foamed latex on a release medium. The dry foam, still on the release paper, is then simultaneously crushed and transfer bonded to the absorbent layer. A second method comprises applying the foam directly on the absorbent layer and crushing if desired. A third method comprises applying unfoamed material on the fabric and then causing foaming by the use of blowing agents then crushing if desired.

8 Claims, No Drawings

METHOD FOR DRESSING A WOUND

This is a continuation-in-part application of U.S. Pat. application Ser. No. 726,716, filed Sept. 24, 1976, now U.S. Pat. No. 4,069,366, which is a divisional of application Ser. No. 394,601, filed Sept. 5, 1973, now U.S. Pat. No. 3,901,240, which is a continuation-in-part of U.S. application Ser. No. 354,062, filed Apr. 24, 1973, now U.S. Pat. No. 3,887,408.

This invention relates to a wound dressing having a top layer (i.e., the layer to be placed next to the skin) of a foam bonded to either a woven, knit or nonwoven absorbent layer. The laminate of the foam and the woven or nonwoven absorbent layer is self-bonded; i.e., no extraneous adhesive is needed.

The wound dressing does not adhere readily to human tissue because of a complete lack of fiber on the exposed surface. Porosity of the foam layer allows wound exudate to penetrate the foam into the absorbent medium. When the dressing is removed, the cohesive strength of the foam lining is so low that any of the foam which becomes permanently entrained during scab formation of a wound will separate away from the remainder of the composite without damaging the wound.

The present invention, by using foams with relatively low cohesive strength and open cells, permits tearing of the foam under moderate elongation but provides good integrity at the low elongations (<50 percent) encountered in normal use.

In general, the invention relates to a flexible absorbent pad comprising a layer of polymeric foam material which is permeable to liquids and a layer of liquid-absorbent material, the improvement in which said polymeric foam material is crushed or uncrushed foam of an addition polymer derived from an aqueous polymer latex having a wet density of from about 0.05 to about 0.5 grams per cc. and a thickness of from about 1 mil to about 50 mils with the horizontal face of the dry foam having approximately 100,000 pores per square inch and a cohesive tearing strength in the range of from about 0.5 to about 10 pounds per linear inch (p.l.i.) in which the foam, when the wound dressing is removed, splits and tears.

Thermoplastic foam is desired since little or no crosslinking is employed, reducing the possibility of skin irritation produced by some crosslinkers.

Standard gauze bandages, i.e., loosely woven 100% cotton in one continuous piece of from 1 to 12 or more layers is the preferred liquid absorbent material.

The term "nonwoven" as employed herein means those fabrics produced from staple fibers or continuous filaments without the use of conventional weaving or knitting operations. For a further description of the type of nonwoven which may be employed, reference is made to U.S. Pat. Nos. 2,931,749; 2,982,682; 3,074,834; 3,101,292 and 3,521,638.

The wet foam can be cast on a release medium, dried to a crushable condition and subsequently adhered to the woven or nonwoven absorbent layer by laminating and simultaneously crushing the foam against the absorbent layer. Alternatively, the wet foam can be cast directly onto the woven or nonwoven absorbent layer, dried and, if desired, subsequently crushed.

The foam initially has a wet foam density of from about 0.05 to about 0.5 grams per cubic centimeter and is applied in a thickness of from about 5 to about 70 mils. The foam is then dried and, if a thermoset plastic, drying without causing thermosetting, crosslinking or vulcanization to a sensibly dry condition. For example, by drying for a period of time of from 1 to 10 minutes at an oven temperature in the range of from about 200° to about 350° F., followed by placing the absorbent material and the surface of the foam together and, if desired, crushing or partially crushing the foam to a thickness of from about 5 percent to about 35 percent of its original dry thickness to afford a foam with a density of from about 0.2 to about 3 g./cc., followed, if necessary, by curing of the foam. In general, the thickness of the dried foam prior to crushing will be less than that of the wet foam due to shrinkage. The shrinkage may be up to 30 percent of the thickness of the wet foam. Suitable moisture contents range from 5 percent to 20 percent in order to qualify as air dry or sensibly dry materials. The criteria as to moisture content is that the foam must be stable enough to be self-bonded to the absorbent material. Crushed foam is defined as that foam which is crushed to a thickness of from about 5 up to about 99 percent of its original dry thickness and preferably from about 20 to about 40 percent of its original dry thickness to afford a crushed foam having a density in the range of from about 0.2 to about 3 g./cc.

To enhance the comfort of the fabric dressings, foam can be used as a topcoat on the textile where it is self-adhering as previously described. The crushed foam imparts a velvet-like texture to the surface of the textile and prevents fibers from coming in contact with the wound. In addition, the foam enhances the surface dryness of the composite. The foam surface can also serve as part of the binding system for the textile permitting reduced usage of conventional binders normally applied by saturation, printing or beater deposition.

Beneficial additives can be incorporated into the foam or the absorbent material or both before or after casting. These include germicidal additives, deodorants, reodorants and fillers which enhance comfort such as talc, or impart fire resistance such as aluminum hydrate. Such fillers also serve to dissipate static electricity for use in operating rooms. Specific medicants include antiseptics such as thimerosal, iodine, nitrofurazone, benzalkonium chloride and the like; antibiotics such as neomycin sulfate, bacitracin and the like; or antiinflammatories such as hydrocortisone and the like; anesthetics such as benzocaine, lidocaine hydrochloride and the like can be employed in the foam layer. Also, rubefacients, softening agents and antipruritics can be employed. It is preferred to incorporate these materials in the foam layer.

For a description of suitable conventional foaming procedures and foam stabilizers and foaming agents, reference is made to Mage, E. W., "Latex Foam Rubber", John Wiley and Sons, New York (1962) and Rogers, T. H., "Plastic Foams", Paper, Reg. Tech. Conf., Palisades Sect., Soc. Plastics Engrs., New York, November 1964. Most common are the alkali metal, ammonia, and amine soaps of saturated or unsaturated acids having, for example, from about 12 to about 22 carbon atoms. Examples of suitable soaps include tallow soaps and coconut oil soaps, preferably the volatile amine or ammonia soaps, so that the volatile portion is vaporized from the foam. Other useful foam stabilizing agents include lauryl sulfatelauryl alcohol, lauryl sulfate-lauric acid, sodium lauryl sulfate, and other commonly used foamed stabilizers or foaming agents.

The latex, when formulated with the foam stabilizer, and optionally suitable pigments and fillers, is readily converted into the foamed state by methods well known to those skilled in the art. The polymer composition is such that excessive thickening of the formulation is not encountered under the acid or alkaline conditions employed to assure the most efficient operation of the foam stabilizing agent. In addition, the copolymer is such that the foam, even when crushed, retains its softness and its flexibility at low temperatures (10° F.) and after curing is nontacky.

Important properties of the copolymer are its relative toughness and flexibility and the minimum film-forming temperature (MFT) of the formulated coating composition, both dependent in large part upon the influence of its monomer composition. The glass transition temperature (Tg) of the copolymer depends upon the selection of monomers and proportions thereof because of their influence on the Tg. "Tg" is a conventional criterion of polymer hardness and is described by Flory, "Principles of Polymer Chemistry", pp. 56 and 57, (1953), Cornell University Press. While actual measurement of the Tg of copolymers may be made, it may be calculated as described by Fox, Bull. Am. Physics Soc. 1, p. 123 (1956). Examples of the Tg of high molecular weight homopolymers and the inherent Tg thereof which permits such calculations are as follows:

| Homopolymer of | Tg ° C. |
|---|---|
| n-octyl acrylate | −80 |
| n-decyl methacrylate | −60 |
| 2-ethylhexyl acrylate | −70 |
| ethyl acrylate | −22 |
| n-butyl acrylate | −54 |
| n-octyl methacrylate | −20 |
| methyl acrylate | − 9 |
| n-tetradecyl acrylate | 20 |
| methyl methacrylate | 105 |
| acrylic acid | 106 |

These or other monomers are blended to give the desired Tg of the copolymer. As is known, for a given number of carbon atoms in the alcohol moiety, the extent and type of branching markedly influences the Tg, the straight chain products giving the lower Tg.

One of the monomers utilized to prepare the water-insoluble addition copolymer is a flexibilizing or "soft" monomer which may be represented by the following formula:

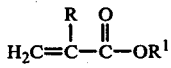
(I)

wherein R is H or alkyl having 1 to 4 carbon atoms and $R^1$ is the straight chain or branched chain radical of a primary or secondary alkanol, alkoxyalkanol or alkylthioalkanol, the alkanol having from 2 to about 14 carbon atoms, the chain length depending upon the identity of R, examples being ethyl methylpropyl, n-butyl, 2-ethylhexyl, heptyl, hexyl, octyl, propyl, 2-methylbutyl, 1-methylbutyl, butoxybutyl, 2-methylpentyl, methoxymethyl, ethoxyethyl, cyclohexyl, n-hexyl, isobutyl, ethylthioethyl, methylthioethyl, ethylthiopropyl, n-octyl, 6-methylnonyl, decyl, dodecyl and the like. When R is alkyl and $R^1$ is alkyl, $R^1$ should have from about 6 to about 14 carbon atoms and when R is H and $R^1$ is alkyl, $R^1$ should have from about 2 to about 12 carbon atoms, in order to qualify as a soft monomer. Also, butadiene may be employed. In addition, copolymers such as those prepared from ethylene or propylene and vinyl acetate may be employed.

In addition to the flexibilizing monomer, the other essential monomers are the "toughening" or "hard" monomers, discussed in greater detail below and including, for example, methyl methacrylate, monovinyl aromatic monomers, certain acrylic acid and/or methacrylic acid esters, and, if used, the monomers having hydroxyl, carboxyl, amino, amido, epoxy, or other functionality described below. The hardness or softness of the acid and other functional monomers is not critical because of the small amounts used. Styrene and vinyltoluene are examples of the monovinyl aromatics.

The unsaturated carboxylic acids, the preferred functional monomers, may be a simple monocarboxylic acid, or may be a half ester of an α, β-unsaturated dicarboxylic acid, and salts thereof. Examples of copolymerizable ethylenically unsaturated monocarboxylic or polycarboxylic acids are sorbic, cinnamic, vinyl furoic, α-chlorosorbic, p-vinylbenzoic, acrylic, methacrylic, maleic, fumaric, aconitic, atropic, crotonic, and itaconic acid, or mixtures thereof, with itaconic acid and the α, β-unsaturated monocarboxylic acids, particularly methacrylic acid and acrylic acid, being preferred. Other copolymerizable acid monomers include the alkyl half esters or partial esters of unsaturated polycarboxylic acids such as of itaconic acid, maleic acid, and fumaric acid, or the partial amides thereof. Preferred half esters are the lower alkyl ($C_1$ to $C_6$) esters such as methyl acid itaconate, butyl acid itaconate, methyl acid fumarate, butyl acid fumarate, methyl acid maleate, and butyl acid maleate. Such partial esters and partial amides are considered to be "α, β-unsaturated monocarboxylic acids", and the term as used herein includes such esters and amides.

For wound bandages, the preferred soft monomers are ethyl acrylate and butyl acrylate. The preferred hard monomers are methyl methacrylate, vinylacetate, methacrylic acid, itaconic acid or acrylic acid.

As noted above, other ethylenically unsaturated copolymerizable monomers present are "hard" or toughening monomers. These may be represented by the formula:

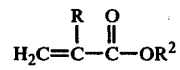

wherein R is as above. $R^2$ is preferably alkyl and is methyl or alkyl having from about 13 to about 20 carbon atoms when R is H, and is alkyl of from about 1 to about 5 carbon atoms or alkyl of from about 15 to about 20 carbon atoms when R is methyl. It can be seen from above that for alkyl acrylates and alkyl methacrylates the Tg at first decreases with an increased chain length of the alkyl group and then the Tg again increases; i.e., both hard and soft monomers are known to occur in each group of esters. Examples of these hard monomers and other hard monomers include: methyl acrylate, vinyl acetate, tetradecyl acrylate, pentadecyl acrylate, methyl methacrylate, ethyl methacrylate, t-butyl acrylate, styrene, vinyltoluene, butyl methacrylate, and pentadecyl methacrylate.

The foam compositions are useful as clear coatings or they may be pigmented with a variety of pigments as set forth hereinafter.

Minimal amounts of the functional monomers discussed heretofore having hydroxy, carboxy, amido or epoxy groups and the like, when used, are beneficial in promoting adhesion and in some cases providing thermosettability. The maximum proportion of such monomers based on total monomers is 10 percent, preferably a maximum of about 5 percent. Excessive amounts of some of these monomers contribute to hydrophilicity of the polymer. If the polymer is excessively hydrophobic or hydrophilic, coatings therefrom may have undesirable properties.

If it is desired to increase the viscosity of these latices, they may be readily thickened with various thickeners such as the water-soluble gums. Thus, the ammonium or lower amine salts of polycarboxylic acids are suitable and typical examples are ammonium polyacrylate and ammonium polymethacrylate, the alkali metal and the mono-, di- or triethylamine salts of polyacrylic and polymethacrylic acids.

The preferred emulsion copolymers for the foam have a molecular weight of between about 70,000 and about 2,000,000 and preferably between about 250,000 and about 1,000,000 and are made by the emulsion copolymerization of the several monomers in the proper properties. Conventional emulsion polymerization techniques are described in U.S. Pat. Nos. 2,754,280 and 2,795,564. Thus, the monomers may be emulsified with an anionic, a cationic or a nonionic dispersing agent, about 0.05 percent to about 10 percent thereof ordinarily being used on the weight of the total monomers. The acid monomer and many of the other functional or polar monomers may be soluble in water so that the dispersing agent serves to emulsify the other monomer or monomers. A polymerization initiator of the free-radical type, such as ammonium or potassium persulfate, may be used alone or in conjunction with an accelerator, such as potassium metabisulfite, or sodium thiosulfate. Organic peroxides such as benzoyl peroxide and t-butyl hydroperoxide are also useful initiators. The initiator and accelerator, commonly referred to as catalyst, may be used in proportions of 0.1 percent to 10 percent each based on the weight of monomers to be copolymerized. The amount, as indicated above, may be adjusted to control the intrinsic viscosity of the polymer. The temperature may be from room temperature to 60° C. or more as is conventional.

Suitable dispersing agents useful in emulsion polymerization include low levels of anionic types such as the sodium salts of the higher fatty acid sulfates, such as that of lauryl alcohol, the higher fatty acid salts, such as the oleates or stearates or morpholine, 2-pyrrolidone, triethanolamine or mixed ethanolamines, or any of the nonionic types, such as ethylene oxide-modified alkyl phenols, of which tertoctyl phenol modified by 20 to 40 ethylene oxide units is representative, ethylene oxide-modified higher fatty alcohols such as lauryl alcohol, containing 20 to 50 ethylene oxide units, similarly modified long-chain mercaptans, fatty acids, amines or the like.

EXAMPLE 1

A copolymer dispersion prepared from 66 parts of ethyl acrylate, 32.7 parts of methyl methacrylate and 1.3 parts of methacrylic acid is compounded in the following formulation:

|  | Product | Solids |
| --- | --- | --- |
| Dispersion (46%) | 71 | 32.3 |
| Thickener | 0.2 | 0.2 |
| Dersertalc 144 | 16.2 | 16.2 |
| Ammonium Stearate | 4.5 | 1.5 |
| Water | 6.8 | — |

| | Product | Solids |
| --- | --- | --- |
| Ammonium Hydroxide (28%) | 1.3 | — |
| Solids - 50.2% | | |

All parts and percentages are by weight unless otherwise stated.

Foam is made by whipping air into the formulation using a Kitchen-Aid Mixer (Model C) to a specific gravity of about 0.22 g./cc. The foam is then cast at 70 mils onto a gauze pad (12 ply) and dried for 10 minutes at 250° F. The dry foam is 50 mils thick. These samples were evaluated. Crushing at 20 psi caused excessive gauze grin-through although the sample would be a satisfactory wound dressing. Crushing at 5 psi and the uncrushed sample afforded a dressing not only aesthetically pleasing but also of sufficient structural integrity to be used as a wound dressing. The foam, though initially stiff, softens when in contact with body heat and is not only comfortable but conforms well.

EXAMPLE 2

Example 1 is repeated using a homopolymer of ethyl acrylate.

The wet foam is placed directly on the knit or gauze. The coated material is dried at 280° F. for 10 minutes and then passed through nip rollers to partially crush the foam.

The following polymer compositions are preferred for bandages.

EXAMPLE 3

87.5% EA/10.5% MMA/2.5% IA with 5.5% by weight of ethoxylated alkyl phenol (40 ethyleneoxide units).

EXAMPLE 4

87.5% EA/10% MMA/2.5% IA with 0.05% sodium dodecylbenzenesulfonate.

EXAMPLE 5

100% EA with 2.3% sodium alkylarylether sulfate.

EXAMPLE 6

66% EA/32.7% MMA/1.3% MAA with 6.0% of ethoxylated octylphenol (40 ethyleneoxide units).

EXAMPLE 7

58% BA/39.5% VA/1.8% IA/0.7% AA with 1.0% sodium lauryl sulfate.

The following explains the abbreviations used in the foregoing examples:
EA — ethyl acrylate
BA — butyl acrylate
IA — itaconic acid
MMA — methyl methacrylate
MAA — methacrylic acid
VA — vinyl acetate

What is claimed is:

1. A method for dressing a wound wherein the improvement comprises applying to said wound a sterile dressing comprising a layer of a foam permeable to liquids adhered to a layer of liquid absorbent material wherein the improvement is that said foam is crushed or uncrushed foam having a wet foam density of from about 0.05 to about 0.5 g./cc. and a dry foam density of from about 0.2 to about 3 g./cc. and a thickness of from about 1 mil to about 70 mils wherein said foam has a cohesive tear strength in the range of from about 0.5 p.l.i. to about 10 p.l.i.

2. The method of claim 1 in which the foam is from about 10 to about 70 mils thick and the absorbent layer is selected from cellulosic textiles of cotton or rayon.

3. The method of claim 2 wherein the sterile wound dressing contains an additive selected from a germicide, deodorant, reodorant, antiseptic, antibiotic, antiinflammatory or anesthetic.

4. The method of claim 1 wherein the foam is thermoplastic.

5. The method of claim 4 wherein the polymer used to prepare the foam is prepared from 87.5% ethyl acrylate; 10.5% methyl methacrylate and 2.5% itaconic acid.

6. The method of claim 4 wherein the polymer used to prepare the foam is prepared from 66% ethyl acrylate, 32.7% methyl methacrylate and 1.3% of methacrylic acid.

7. The method of claim 4 wherein the polymer used to prepare the foam is prepared from ethyl acrylate.

8. The method of claim 4 wherein the polymer used to prepare the foam is prepared from butyl acrylate.

* * * * *